United States Patent [19]

Itoh et al.

[11] Patent Number: 5,367,001
[45] Date of Patent: Nov. 22, 1994

[54] IMPRESSION COMPOSITION

[75] Inventors: Kunio Itoh; Yoshio Inoue, both of Annaka; Hironao Fujiki, Takasaki; Masachika Yoshino, Annaka, all of Japan

[73] Assignee: Shin-Etsu Chemical Co., Ltd., Tokyo, Japan

[21] Appl. No.: 48,577

[22] Filed: Apr. 9, 1993

Related U.S. Application Data

[63] Continuation of Ser. No. 501,715, Mar. 30, 1990, abandoned.

Foreign Application Priority Data

Mar. 31, 1989 [JP] Japan .................................. 1-82531

[51] Int. Cl.$^5$ .............................................. C08K 5/15
[52] U.S. Cl. .................................. 523/109; 524/751; 524/780; 524/784; 524/788; 524/861
[58] Field of Search ............... 523/109; 524/751, 784, 524/788, 780, 861

[56] References Cited

U.S. PATENT DOCUMENTS

| | | | |
|---|---|---|---|
| 4,248,750 | 2/1981 | Murakami et al. | 260/29.1 SB |
| 4,565,714 | 1/1986 | Koshar | 427/54.1 |
| 4,877,854 | 10/1989 | Hattori et al. | 528/15 |
| 4,879,339 | 11/1987 | Yoshino et al. | 524/740 |

FOREIGN PATENT DOCUMENTS 55-078055  6/1980  Japan .

*Primary Examiner*—Ralph H. Dean
*Attorney, Agent, or Firm*—Oblon, Spivak, McClelland, Maier & Neustadt

[57] ABSTRACT

A impression composition comprising:
(A) a polyether polymer having at least two alkenyl groups in its molecule,
(B) a polyorganohydrogensiloxane having at least three silicon-bonded hydrogen atoms in its molecule,
(C) a platinum catalyst,
(D) an inorganic filler, and
(E) an antioxidant.

This composition of has hydrophilic nature and a small cure shrinkage; hence it enables precise impression in a wet environment like in a mouth.

9 Claims, No Drawings

IMPRESSION COMPOSITION

This application is a continuation of application Ser. No. 07/501,715, filed on Mar. 30, 1990, now abandoned.

BACKGROUND OF THE INVENTION

1. Field of the Invention

The present invention relates to a impression composition, in particular, to a impression composition having good hydrophilic nature and a small cure shrinkage.

2. Description of the Prior Art

Heretofore, for various kinds of impression materials including dental impression materials, materials containing as a main ingredient a polyether (Japanese preexamination Patent Publication (KOKAI) No. 55538/1986), polysulfide, and a silicone have been used.

However, of the above materials, polyethers have hydrophilic nature, but has the disadvantage that its cure shrinkage is too large. The polysulfide has a strong unpleasant smell. Although the silicone has a good impression performance, it has poor hydrophilic nature; hence it has the disadvantage that when used for dental purposes, impression performance at portions wet with saliva or blood is worse.

Therefore, it has been proposed to impart hydrophilic nature to silicone materials by adding a polyether modified siloxane or a fluorine-containing surfactant. However, this may cause blooming of the additive or liquid separation during processing on a molding device.

SUMMARY OF THE INVENTION

In order to remove the disadvantages of the prior arts above, the present invention provides a impression composition comprising:
- (A) a polyether polymer having at least two alkenyl groups in its molecule,
- (B) a polyorganohydrogensiloxane having at least three silicon-bonded hydrogen atoms in its molecule,
- (C) a platinum catalyst,
- (D) an inorganic filler, and
- (E) an antioxidant.

The impression composition of the present invention has hydrophilic nature and a small cure shrinkage. Therefore, the composition enables precise impression in a wet environment like in a mouth; it is useful as various kinds of impression materials or mold-taking materials including dental impression materials.

DETAILED DESCRIPTION OF PREFERRED EMBODIMENTS

(A) Polyether polymer

First, the polyether polymer having at least two alkenyl groups in its molecule of the component (A) has hydrophilic nature itself, and is a main component that undergoes curing to get rubbery. The polyether polymer herein means a polymer that has a polyether chain composed of two or more alkylene oxide units containing from 2 to 4 carbon atoms exemplified by $-CH_2CH_2O-$, $-CH_2CH_2CH_2O-$,

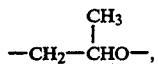

and $-CH_2CH_2CH_2CH_2O-$. These alkylene oxide units may be contained in the polyether chain singly or in combination of two or more kinds.

The hydrophilic nature of an alkylene oxide unit generally increases with decrease in the number of carbon atoms contained therein. However, a polyether polymer whose polyether chain is composed of the $-CH_2CH_2O-$ unit only, is so hydrophilic that it can swell with water extremely; hence precise impression can be performed with difficulty. In that case, incorporation of suitable amounts of moieties with poor hydrophilic nature such as diorganosiloxane chain can decrease the hydrophilic nature to a suitable level. On the other hand, a polyether polymer whose polyether chain is composed of the $-CH_2CH_2CH_2CH_2O-$ unit only, has insufficient hydrophilic nature. Therefore, the polyether polymer preferably contains one or more kinds of alkylene oxide units suitably such that it has suitable hydrophilic nature as a whole. In general, the polyether polymer of the component desirably contains at least one unit selected from $-CH_2CH_2O-$ and $-CH_2CHCH_3O-$ in order to acquire suitable hydrophilic nature and swell characteristics.

Preferred polyether polymers include one whose polyether chain consists of $-CH_2CHCH_3O-$ unit only, and one whose polyether chain contains $-CH_2CH_2O-$ unit and $-CH_2CHCH_3O-$ unit like copolymers of ethylene oxide and propylene oxide.

Also preferred is the polyether polymer of which the polyether chain consists of the $-CH_2CH_2O-$ unit only but which further contains a proper number of diorganosiloxane units, so that the polyether polymer has suitable hydrophilic nature and swell characteristics as a whole.

The polyether polymer of the component (A) preferably contains from 10 to 1,000, more preferably from 20 to 500, of the repeated alkylene oxide units described above because it exhibits fluidity before cure and exhibits good elastomeric properties after cure as an impression material for dental use, for instance.

The component (A) contains at least two alkenyl groups. These alkenyl groups are a necessary functional group to undergo addition reaction with Si-H bonds contained in the component (B) described later, thereby the composition being cured. The alkenyl group includes, for example, the vinyl, allyl, butenyl, vinyldimethylsilyl, divinylmethylsilyl, trivinylsilyl, and allyldimethylsilyl groups. Among these, for example, preferred are the allyl group and vinyldimethylsilyl group $(CH_2=CH-(CH_3)_2Si-)$.

Such component (A) includes, for example, the compounds having the following formulas:

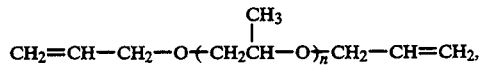

and

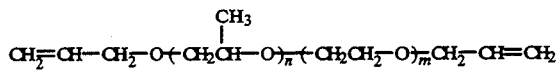

in the above formulas, m is an integer of from 0 to 1,000, n is an integer of from 0 to 1,000, and m+n ranges from 1 to 1,000. Methods for producing a polyether polymer terminated with the ally groups at both ends like the above compounds are well known in the art. The first compound and the second compound above are commercially available from Nippon Oil & Fat Co., Ltd. under the tradenames UNILUBE DP-2300s (average MW: 2300) and UNILUBE 50 MA-230S, respectively.

The component (A) may contain a silicon atom so that its reactivity with the polyorganohydrogensiloxane of the component (B) may be improved. Such component (A) may be a silane or a diorganopolysiloxne exemplified by the following.

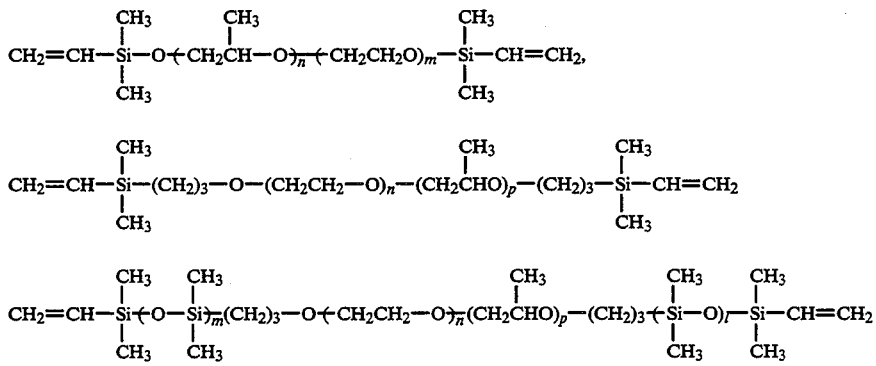

in the above formulas, 1 and m are each an integer of from 1 to 30, n is an integer of from 1 to 1,000, p is an integer of from 0 to 1,000, provided that n+p ranges from 1 to 1,000. Polyether polymers terminated with vinyldiorganosilyl groups or divinylorganosilyl groups at both ends like the above first two compounds can be synthesized by methods known in the art. For example, such a polyether polymer is prepared by subjecting a corresponding polyalkyleneoxide terminated with hydroxyl groups at its both ends and an organomonochlorosilane containing an intended triorganosilyl group (e.g., $CH_2=CH-(CH_3)_2Si-$ and $(CH_2=CH)_2CH_3-Si-$) to dehydrochlorination in the presence of a neutralizing agent such as hexamethyldisilazane. Polyether polymers terminated with vinyl-containing siloxy groups at both ends like the above third compound can be also prepared by methods known in the art. For example, first, an polyalkyleneoxide terminated with ally groups is reacted with a diorganochlorosilane (e.g., $HSi(CH_3)Cl$) in the presence of a platinum catalyst, to produce a polyether terminated with chlorosilyl groups (e.g.,-$Si(CH_3)_2Cl$). This polyether and a vinylsiloxy-containing siloxane terminated with the hydroxyl group at one end exemplified by

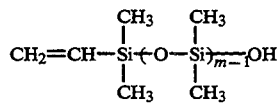

where m is an integer of from 1 to 30, are then subjected to dehydrochlorination in the presence of a neutralizing agent such as 1,3-divinyl-1,1,3,3-tetramethyldisilazane to produce the desired compound.

Incidentally, curing of a polyether polymer containing repeated alkylene oxide units like the component (A) may produce a too hard cured product. This problem can be overcome by adding a suitable amount of a silicone oil having an alkenyl group such as the vinyl group or the allyl group at its one end or a silicone oil with no functional group. These are exemplified by the following formulas:

and

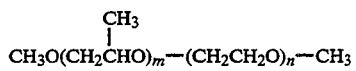

where m and n are each an integer of 0 or more, provided m+n ranges from 1 to 1,000. These compounds are commercially available under tradename, UNIOX MA-500 and as one of UNIOX series, respectively, from Nippon Oil & Fat Co., Ltd.

Component (B)

The polyorganohydrogensiloxane of the component (B) undergoes addition reaction with the component (A) and thereby serves to cause crosslinking or cure of the present composition. The component (B) may be any polyorganohydrogensiloxane conventionally used for addition-type silicone elastomers. A typical example of the component (B) is a compound having the following average unit formula:

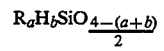

wherein R represents a $C_1$ to $C_7$ alkyl group, the phenyl group, a haloalkyl group, a represents a number of $1<a<2$, and b represents a number of $0<b<1$, provided that $1<a+b<2.7$, and containing at least three Si—H bonds in the molecule.

More specifically, the polyorganohydrogensiloxane includes the compounds having the formulas (i)–(viii):

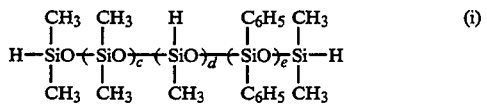

where c and e are an integer of 0 or more, and d is an integer of 1 or more,

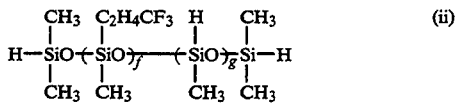

where f is an integer of 0 or more, and g is an integer or more, and that its compatibility with the component (A) may be enhanced. Such a polyorganohydrogensiloxane is exemplified by the following.

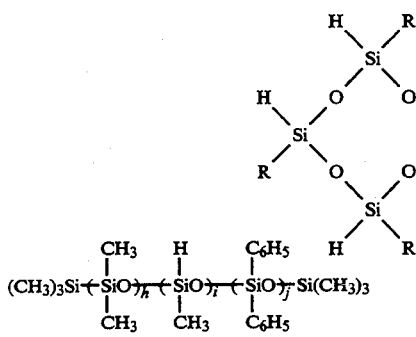
(iii)

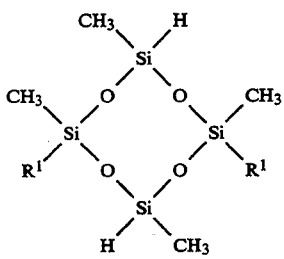

where h and j are an integer of 0 or more, and i is an integer of 1 or more,

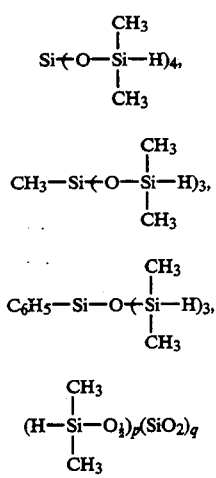

wherein p and q are each more than 0, provided p+q=1, and wherein $R^1$ represents a hydrogen atom, or an $C_1$-$C_8$ monovalent hydrocarbon group such as an alkyl group and an aryl group, or a triorganosiloxy group such as the trimethylsiloxy group. Among these compounds, preferred are the compound of the formula (i) wherein c+d+e is 300 or less, the compound of the formula (ii) wherein f+g is 300 or less, and the compound of the formula (iii) wherein h+i+j is 300 or less.

The component (B) is preferably contained in the composition such that the molar ratio of the Si—H bonds contained in the component (B) to the alkenyl groups contained in the component (A) ranges from 0.5 to 5, more preferably from 0.8 to 3.

Incidentally, the component (B) may contain a polyether structure in a suitable amount in its structure so that its compatibility with the component (A) may be enhanced. Such a polyorganohydrogensiloxane is exemplified by the following.

wherein R may be the same or different, and each represent the methyl or the trimethylsilyl group, and m and n are each an integer of from 0 to 500, provided m+n ranges from to 500.

Component (C)

The platinum catalyst of the component (C) may be any platinum catalyst conventionally used for normal hydrosilylation reaction. It includes, for example, chloroplatinic acid, alcohol-modified chloroplatinic acids, platinum-vinylsiloxane complexes, and the like. Preferred are platinum catalysts containing no or little chlorine like the platinum-vinylsiloxanes inasmuch as the storability of the composition can be improved.

The component (C) is contained in the composition preferably in an amount of from 1 to 1,000 ppm, more preferably from 10 to 200 ppm, based on the amount of the component (A). If the amount of the component (C) is too small, crosslinking reaction of the components (A) and (B) may not proceed sufficiently. If the amount of the component (C) is too large, not only the control of crosslinking reaction become difficult, but also depolymerization of polysiloxane structure may be possibly caused. Moreover, an excess of the platinum catalyst may promote the deterioration by oxidation of the polyether polymer of the component (A), thereby making easier formation of by-products such as aldehydes, and further may lower the cure rate of the composition, which may lead to incomplete cure in an extreme case.

Component (D)

The inorganic filler of the component (D) may be any known fillers used conventionally for impression compositions of this type, including, for example, fine powdery silica such as fumed silica and precipitated silica, quartz powder, glass fiber, carbon powder, iron oxide, titanium oxide, zinc oxide, calcium carbonate, magnesium carbonate, and the like.

The component (D) is normally contained in the composition in an amount of from 5 to 50 parts by weight per 100 parts by weight of the component (A). If the amount of the component (D) is too small, cure shrinkage of the composition is large. If the amount of the component (D) is too large, the composition has an excessively high viscosity and therefore has poor workability.

Component (E)

The antioxidant of the component (E) is added to the composition in order to ensure long-term storability of the composition, and to control generation of stimulative smell so that the composition may not give unpleasant feeling to patients when used. That is, the polyether polymer of the component (A) may deteriorate by oxidation with lapse of time, and the platinum catalyst of the component (B) promotes the oxidation. Further, the component (C) per se may deteriorate by oxidation, which results in lowering of the cure rate of the composition. The component (E) is added to eliminate these disadvantages by preventing oxidation of the components, and can thereby prevent the patient from feeling a pain or unpleasant smell.

The antioxidant may be any one that is effective against oxygen radials, has no bad influence on human bodies, and does not act as a catalyst poison against hydrosilylation reaction catalyzed by the platinum catalyst of the component (C). Such antioxidants include, for example, vitamin E (i.e., tocophero), BHT (i.e., 2,6-di-tert-butyl-p-hydroxytoluen), erythorbic acid, sodium erythorbate, butylhydroxyanisole, and propyl gallate.

The component (E) is added to the composition normally in an amount of 10 ppm or more, preferably from 50 to 5,000 ppm, based on the component (A).

Other components

The component (A) has a large water absorption because it often has an alcoholic residual group at its terminal and has a hydrophilic nature due to its polyether chain. Consequently, dehydrogen reaction is liable to occur between Si—H bonds and water or the alcoholic residual group to form bubbles in the resulting cured product. In order to prevent this problem, the composition may contain some additives such as, for example, hydrogen storage alloy, a palladium compound, or these substances supported on a carrier such as alumina, carbon, and silica. Potassium acetate is also effective in spite of its slight smell.

Further the composition may optionally contain a colorant, for example, titanium oxide, iron oxide, cobalt aluminate, pigments such as quinacridone pigments and phthalocyanine pigments, dyes such as anthraquinone dyes and azo dyes, and a perfume.

Preparation and uses

The composition of the present invention can be cured within a short time (e.g., several minutes) even at room temperature by mixing the components described above in prescribed amounts by a suitable method when used.

The composition has wetting characteristics available for hydrous materials and hydrophilic materials during or after curing, due to the hydrophilic nature of the component (A) itself. Accordingly, the composition is particularly useful as a dental impression material for which precise impression performance is required in a wet environment. The composition can also be used as a mold-taking material which requires hydrophilic nature, and can be also used extensively for other diverse purposes.

EXAMPLES

Synthesis Example 1

In a 3 liter flask, 100 g of poly(propylene oxide/ethylene oxide) terminated with the hydroxy group at its both ends and having a viscosity of 2,000 cP at 25° C. was placed, and 10 g of vinyldimethylchlorosilane was added dropwise in the flask in the presence of hexamethyldisilazane at room temperature, followed by mixing. The mixture thus obtained was filtered, and the filtrate was placed in a flask. After the inner atmosphere of the flask was replaced with nitrogen, stripping was carried out under 1 torr, at 100° C., thereby a polymer being obtained.

The polymer was identified from data of GPC analysis an so on as having the structure below on average.

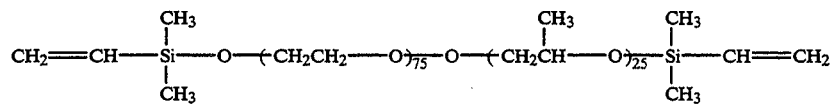

This polymer is hereinafter referred to as Polyether polymer (a).

Synthesis Example 2

To 500 g of polypropylene oxide terminated with the allyl group at its both ends and having a viscosity of 3,000 cP at 25° C. (this polymer is hereinafter referred to as Polyether polymer (b)), 0.1 g of a platinum catalyst with a platinum content of 2%, was added. The entire mixture thus obtained was placed in a 3 liter flask equipped with a condenser. The mixture was then heated at 100° C. under stirring for about 4 hours while 25 g of dimethylchlorosilane was added thereto dropwise from a dropping funnel.

Subsequently, the pressure inside the flask was reduced to 1 torr while the temperature was maintained at 100° C. and then stripping was carried out Thereafter, the temperature was decreased to room temperature. After another dropping funnel was provided for the flask, 25 g of vinyldimethylhydroxysilane and 50 g of 1,3-divinyl-1,1,3,3-tetramethyldisilazane were added dropwise and mixed into the mixture. After the inside of the flask was replaced with nitrogen, stripping was carried out under 1 torr, at 100° C., followed by filtration to give a polymer having the following structure.

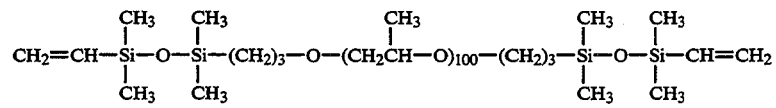

This polymer is hereinafter referred to as Polyether polymer (c). Examples 1-3, Comparative Example 1

The Polyether polymer (a), (b) or (C) described above was used as a component (A), and Components (B) (E) were added to the Component (A) as given in Table 1. The mixture was thoroughly kneaded, and then cured at room temperature. Properties of the cured products obtained are given in Table 1.

TABLE 1

|  | Example 1 | Example 2 | Example 3 | Comparative Example 1 |
|---|---|---|---|---|
| Composition (parts by weight) | | | | |
| (A) Polyether polymer | | | | |
| Kind | (b) | (a) | (c) | (b) |
| Amount | 100 | 100 | 100 | 100 |
| (B) Crosslinking agent*1 | 10 | 10 | 10 | 10 |
| (C) Pt-vinylsiloxane complex | 0.2 | 0.2 | 0.2 | 0.2 |
| (D) Aerosil R-812*2 | 5 | 5 | 5 | 5 |
| (E) Vitamin E | 0.01 | 0.01 | 0.01 | — |
| Properties of composition or cured product | | | | |
| Appearance of cured product | good | good | good | good |
| Curability after accelerated deterioration*3 | good | good | good | cure slowed |
| Shrinkage (%) | 10 | 10 | 10 | 10 |
| Contact angle of water*4 | 68 | 43 | 70 | 65 |

Remarks:
*1 The crosslinking agent has the structure below on average:

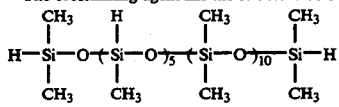

*2 Hydrophobic fumed silica supplied by Degussa.
*3 A composition containing no component (B) was subjected to accelerated deterioration at 60° C. for 3 weeks, and thereafter a component (B) was added to the composition. The resulting composition was tested for curability.
*4 The contact angle of water on a cured product was measured after 3 minutes by means of a goniometer.

We claim:

1. A dental impression composition comprising:

(A) a polyether polymer having at least two alkenyl groups in its molecule, (B) a polyorganohydrogensiloxane having at least three silicone-bonded hydrogen atoms in its molecule, selected from the compounds represented by the formulas:

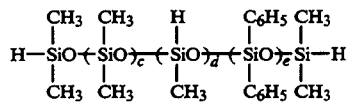

where c and e are an integer of 0 or more, and d is an integer of 1 or more,

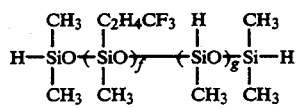

where f is an integer of 0 or more, and g is an integer of 1 or more, or

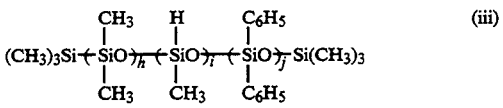

where h and j are an integer of 0 or more, and i is an integer of 3 or more;

(C) a platinum catalyst, (D) an inorganic filler, and (E) vitamin E.

2. The dental impression composition of claim 1, wherein the polyether polymer of the component (A) has a polyether chain composed of —$CH_2CHCH_3O$— units, or of —$CH_2CHCH_3O$— units and —$CH_2CH_2O$— units.

3. The dental impression composition of claim 1, wherein the polyether polymer of the component (A) is composed of from 10 to 1,000 alkylene oxide units.

4. The dental impression composition of claim 1, wherein the inorganic filler of the component (D) is selected from the group consisting of powdery silicas, quartz powder, glass fiber, carbon powder, iron oxide, titanium oxide, zinc oxide, calcium carbonate, and magnesium carbonate.

5. The dental impression composition of claim 1 which contains the component (B) in an amount such that the molar ratio of the Si—H bonds in the component (B) to the alkenyl groups in the component (A) ranges from 0.5 to 5, the component (C) in an amount of from 1 to 1,000 ppm based of the component (A), the component (D) in an amount of from 5 to 500 parts by weight per 100 parts by weight of the component (A), and the component (E) in an amount of not less than 10 ppm based on the amount of the component (A).

6. A dental impression cured product obtained by curing the impression composition comprising the components (A), (B), (C), (D), and (E) as claimed in claim 1.

7. The dental impression composition of claim 5, wherein said molar ratio of the Si—H bonds in the component (B) to the alkenyl groups in the component (A) ranges from 0.8 to 3.

8. The dental impression composition of claim 1, which contains component (C) in an amount of from 10 to 200 ppm based on the component (A).

9. The dental impression composition of claim 1, which contains component (E) in an amount of from 50 to 5,000 ppm based on the amount of the component (A).

* * * * *